US009517128B2

(12) United States Patent
McAlpine et al.

(10) Patent No.: US 9,517,128 B2
(45) Date of Patent: Dec. 13, 2016

(54) MULTI-FUNCTIONAL HYBRID DEVICES/STRUCTURES USING 3D PRINTING

(71) Applicants: Michael C. McAlpine, Lawrenceville, NJ (US); Manu Sebastian-Mannoor, Princeton, NJ (US); Yong Lin Kong, Princeton, NJ (US); Blake N Johnson, Plainsboro, NJ (US)

(72) Inventors: Michael C. McAlpine, Lawrenceville, NJ (US); Manu Sebastian-Mannoor, Princeton, NJ (US); Yong Lin Kong, Princeton, NJ (US); Blake N Johnson, Plainsboro, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 199 days.

(21) Appl. No.: 14/203,523

(22) Filed: Mar. 10, 2014

(65) Prior Publication Data

US 2014/0257518 A1 Sep. 11, 2014

Related U.S. Application Data

(60) Provisional application No. 61/774,913, filed on Mar. 8, 2013.

(51) Int. Cl.
*A61F 2/70* (2006.01)
*B29C 45/16* (2006.01)
(Continued)

(52) U.S. Cl.
CPC .............. *A61F 2/18* (2013.01); *A61L 27/14* (2013.01); *A61L 27/38* (2013.01); *A61L 27/54* (2013.01);
(Continued)

(58) Field of Classification Search
CPC .............. A61F 2/70; A61B 5/01; A61B 5/141
(Continued)

(56) References Cited

U.S. PATENT DOCUMENTS 8,409,655 B2 * 4/2013 Uibel ...................... A61C 5/08
427/2.27
2012/0265034 A1 * 10/2012 Wisniewski ....... A61B 5/14735
600/309

(Continued)

OTHER PUBLICATIONS

Lavine, M. et al., "If I Only Had a . . . ", Science. vol. 295. Feb. 2002.
(Continued)

*Primary Examiner* — Suzette J Gherbi
(74) *Attorney, Agent, or Firm* — Meagher Emanuel Laks Goldberg & Liao, LLP

(57) ABSTRACT

A bioelectronic device and method of making is disclosed. The device includes a scaffold formed via 3D printing. The device also includes a biologic and an electronic device formed via 3D printing, the biologic and electronic device being interweaved with or coupled to the scaffold. The electronic component may e.g., include at least one of hard conductors, soft conductors, insulators and semiconductors. The scaffold may be formed of at least one of synthetic polymers and natural biological polymers. The biologic may include at least one of animal cells, plant cells, cellular organelles, proteins and DNA (including RNA).

21 Claims, 17 Drawing Sheets

(51) Int. Cl.
A61F 2/50 (2006.01)
A61F 2/18 (2006.01)
B29C 67/00 (2006.01)
B33Y 80/00 (2015.01)
A61L 27/14 (2006.01)
A61L 27/38 (2006.01)
A61L 27/54 (2006.01)

(52) U.S. Cl.
CPC .......... *B29C 67/0059* (2013.01); *B33Y 80/00* (2014.12); *A61F 2002/183* (2013.01); *A61L 2300/252* (2013.01); *A61L 2300/258* (2013.01); *H04R 2225/77* (2013.01)

(58) Field of Classification Search
USPC ................................................ 623/24, 23.72
See application file for complete search history.

(56) References Cited

U.S. PATENT DOCUMENTS

| | | | |
|---|---|---|---|
| 2013/0012612 A1* | 1/2013 | Houbertz-Krauss | C07H 9/04 522/89 |
| 2013/0056910 A1* | 3/2013 | Houbertz-Krauss | B33Y 30/00 264/401 |
| 2013/0193621 A1* | 8/2013 | Daya | A61K 9/70 264/401 |
| 2013/0307848 A1* | 11/2013 | Tena | G06T 17/20 345/420 |
| 2014/0319734 A1* | 10/2014 | Voit | B29C 45/00 264/400 |
| 2014/0330421 A1* | 11/2014 | Wu | G06T 17/00 700/119 |
| 2014/0350184 A1* | 11/2014 | Wang | C08J 7/12 525/54.2 |
| 2014/0357964 A1* | 12/2014 | Wisniewski | A61B 5/1451 600/301 |
| 2015/0079362 A1* | 3/2015 | Yang | C08F 267/06 428/209 |
| 2015/0313704 A1* | 11/2015 | Thavandiran | C12M 21/08 623/23.72 |
| 2015/0314039 A1* | 11/2015 | Dean | A61L 27/50 522/18 |
| 2015/0376248 A1* | 12/2015 | Kurland | C07K 14/43586 430/9 |
| 2015/0380355 A1* | 12/2015 | Rogers | H01L 23/538 257/773 |

OTHER PUBLICATIONS

Craelius, W., "The Bionic Man: Restoring Mobility", Science, 295, Feb. 2002.
Green, D. W., "Tissue Bionics; examples in biomimetic tissue engineering", Biomed. Mater., Aug. 3, 2008.
Tian, B.; et al., "Macroporous nanowire nanoelectronic scaffolds for synthetic tissues", Nat. Mater., Aug. 11, 2012.
Timko, B. P., "Electrical Recording from Hearts with Flexible Nanowire Device Arrays", Nano Lett., Jan. 9, 2009.
Nguyen, T. D. et al., "Piezoelectric nanoribbons for monitoring cellular deformations", Nat.Nanotechnol., Jul. 7, 2012.
Viventi, J. et al., "Flexible, foldable, actively multiplexed, high-density electrode array for mapping brain activity in vivo" Nat. Neurosci., Dec. 14, 2011.
Kim, D. H. et al., "Epidermal Electronics", Science, 333, Sep. 2011.
Mannoor, M. S. et al., "Graphene-based wireless bacteria detection on tooth enamel", Nat. Commun., Mar. 3, 2012.
Pampaloni, F.; Reynaud, E. G.; Stelzer, E. H. "The third dimension bridges the gap between cell culture and live tissue", Nat. Rev. Mol. Cell Biol., Oct. 8, 2007.
Langer, R.; Vacanti, J. P., Tissue Engineering, Science, 260, May 1993.

Langer, R.; Vacanti, J. P., "Gene Therapy", Sci. Am., 273, 1995.
Jayawarna, V.; Ali, M.; Jowitt, T. A.; Miller, A. F.; Saiani, A.; Gough, J. E.; Ulijn, R. V. "Nanostructured Hydrogels for Three-Dimensional Cell Culture Through Self-Assembly of Fluorenylmethoxycarbonyl—Dipeptides", Adv. Mater., 18, 2006.
Lee, M. Y.; Kumar, R. A.; Sukumaran, S. M.; Hogg, M. G.; Clark, D. S.; Dordick, J. S., "Three-dimensional cellular microarray for high-throughput toxicology assays", Proc. Natl. Acad. Sci. U.S.A., 105, Jan. 2008.
Mapili, G.; Lu, Y.; Chen, S.; Roy, K. J., "Laser-Layered Microfabrication of Spatially Patterned Functionalized Tissue-Engineering Scaffolds", Biomed. Mater. Res., Part B, 75, Jul. 2005.
Marler, J. J.; Upton, J.; Langer, R.; Vacanti, J. P., "Transplantation of cells in matrices for tissue regeneration", Adv. Drug Delivery. Rev., 33, 1998.
Shieh, S. J.; Terada, S.; Vacanti, J. P., "Tissue engineering auricular reconstruction: in vitro and in vivo studies", Biomaterials, 25, 2004.
Napolitano, A. P.; Dean, D. M.; Man, A. J.; Youssef, J.; Ho, D. N.; Rago, A. P.; Lech, M. P.; Morgan, J. R., "Scaffold-free three-dimensional cell culture utilizing micromolded nonadhesive hydrogels", Bio Techniques, 43 (494), Oct. 2007.
Jamal, M.; Kadam, S. S.; Xiao, R.; Jivan, F.; Onn, T. M.; Fernandes, R.; Nguyen, T. D.; Gracias, D. H., "Bio-Origami Hydrogel Scaffolds Composed of Photocrosslinked PEG Bilayers", Adv. Healthcare Mater., 2013.
Chang, S. C.; Tobias, G.; Roy, A. K.; Vacanti, C. A.; Bonassar, L. J., "Tissue Engineering of Autologous Cartilage for Craniofacial Reconstruction by Injection Molding", Plast. Reconstr. Surg., 112, Sep. 2003.
Khademhosseini, A.; Langer, R.; Borenstein, J.; Vacanti, J. P., "Microscale technologies for tissue engineering and biology", Proc. Natl. Acad. Sci. U.S.A., 103, Feb. 2006.
Atala, A., "Engineering organs", Curr. Opin. Biotechnol., Nov. 20, 2009.
Cao, Y.; Vacanti, J. P.; Paige, K. T.; Upton, J.; Vacanti, C. A., "Transplantation of Chondrocytes Utilizing a Polymer-Cell Construct to Produce Tissue-Engineered Cartilage in the Shape of a Human Ear", Plast. Reconstr. Surg., 100, Aug. 1997.
Symes, M. D.; Kitson, P. J.; Yan, J.; Richmond, C. J.; Cooper, G. J.; Bowman, R. W.; Vilbrandt, T.; Cronin, L., "Integrated 3D-printed reactionware for chemical synthesis and analysis", Nature Chem., May 4, 2012.
Jones, N., "Three-Dimensional Printers Are Opening Up New Worlds to Research", Nature, 487, Jul. 2012.
Reiffel, A. J.; Kafka, C.; Hernandez, K. A.; Popa, S.; Perez, J. L.; Zhou, S.; Pramanik, S.; Brown, B. N.; Ryu, W. S.; Bonassar, L. J.; Spector, J. A., "High-Fidelity Tissue Engineering of Patient-Specific Auricles for Reconstruction of Pediatric Microtia and Other Auricular Deformities", PLoS One, Feb. 8, 2013.
Villar, G.; Graham, A. D.; Bayley, H., "A Tissue-Like Printed Material", Science, 340, Apr. 2013.
Yeong, W. Y.; Chua, C. K.; Leong, K. F.; Chandrasekaran, M., "Rapid prototyping in tissue engineering: challenges and potential", Trends Biotechnol., Dec. 22, 2004.
Cohen, D. L; Malone, E.; Lipson, H.; Bonassar, L. J., "Direct Freeform Fabrication of Seeded Hydrogels in Arbitrary Geometries", Tissue Eng., 12, 2006.
Khalil, S.; Nam, J.; Sun, W., "Multi-nozzle deposition for construction of 3D biopolymer tissue scaffolds", Rapid Prototyping J., 11, 2005.
Xu, T.; Binder, K. . K W.; Albanna, M. Z.; Dice, D.; Zhao, W.; Yoo, J. J.; Atala, A., "Hybrid printing of mechanically and biologically improved constructs for cartilage tissue engineering applications", Biofabrication, 5, 2013.
Malone, E.; Berry, M.; Lipson, H., "Freeform fabrication and characterization of Zn-air batteries", Rapid Prototyping J., 14, 2008.
Ahn, B. Y.; Duoss, E. B.; Motala, M. J.; Guo, X.; Park, S. I.; Xiong, Y.; Yoon, J.; Nuzzo, R. G.; Rogers, J. A.; Lewis, J. A., "Omnidirectional Printing of Flexible, Stretchable, and Spanning Silver Microelectrodes", Science, 323, Mar. 2009.
Wu, W.; DeConinck, A.; Lewis, J. A., "Omnidirectional Printing of 3D Microvascular Networks", Adv. Mater., 23, 2011.

(56) References Cited

OTHER PUBLICATIONS

Someya, T.; Sekitani, T.; Iba, S.; Kato, Y.; Kawaguchi, H.; Sakurai, T., "A large-area, flexible pressure sensor matrix with organic field-effect transistors for artificial skin applications", Proc. Natl. Acad. Sci. U.S.A., 101, Jul. 2004.

Bichara, D. A.; O'Sullivan, N. A.; Pomerantseva, I.; Zhao, X.; Sundback, C. A.; Vacanti, J. P.; Randolph, M. A., "The Tissue-Engineered Auricle: Past, Present, and Future", Tissue Eng., Part B, 18, 2012.

Marijnissen, W. J. C. M.; van Osch, G. J. V. M; Aigner, J.; van der Veen, S. W.; Hollander, A. P.; Verwoerd-Verhoef, H. L.; Verhaar, J. A. N., "Alginate as a chondrocyte-delivery substance in combination with a non-woven scaffold for cartilage tissue engineering", Biomaterials, 23, 2002.

Dobratz, E. J.; Kim, S. W.; Voglewede, A.; Park, S. S., "Injectable Cartilage", Arch. Facial Plast. Surg., 11, 2009.

Kelly, D. J.; Crawford, A.; Dickinson, S. C.; Sims, T. J.; Mundy, J.; Hollander, A. P.; Prendergast, P. J.; Hatton, P. V., "Biochemical markers of the mechanical quality of engineered hyaline cartilage", J. Mater. Sci. Mater. Med., 18, 2007.

Li, C.; Pruitt, L. A.; King, K. B., "Nanoindentation differentiates tissue-scale functional properties of native articular cartilage", J. Biomed. Mater. Res. A, 78, Jan. 2006.

Hott, M. E.; Megerian, C. A.; Beane, R.; Bonassar, L. J., "Fabrication of Tissue Engineered Tympanic Membrane Patches Using Computer-Aided Design and Injection Molding", Laryngoscope, 114, Jul. 2004.

Young-Yo, K.; Sah, R. L. Y.; Doong, J. Y. H.; Grodzinsky, A., "Fluorometric Assay of DNA in Cartilage Explants Using Hoechst 33258", J. Anal. Biochem., 174, Mar. 1988.

Stegemann, H.; Stalder, K., "Determinatoin of Hydroxyproline", Clin. Chim. Acta, Jul. 18, 1967.

Enobakhare, B. O.; Bader, D. L.; Lee, D. A., "Quantification of Sulfated Glycosaminoglycans in Chondrocyte/Alginate Cultures, by Use of 1,9-Dimethylmethylene Blue", Anal. Biochem., 243, Jul. 1996.

Schmitz, N.; Laverty, S.; Kraus, V. B.; Aigner, T., "Basic methods in histopathology of joint tissues", Osteoarthr. Cartilage, May 18, 2010.

Baker, B. M.; Nathan, A. S.; Huffman, G. R.; Mauck, R. L., "Tissue engineering with meniscus cells derived from surgical debris", Osteoarthr. Cartilage, 17, 2009.

Ebenstein, D. M.; Pruitt, L. A., "Nanoindentation of biological materials" Nano Today, Aug. 1, 2006.

Oliver, W. C.; Pharr, G. M., "An improved technique for determining hardness and elastic modulus using load and displacement sensing indentation experiments", J. Mater. Res., Jan. 7, 1992.

* cited by examiner

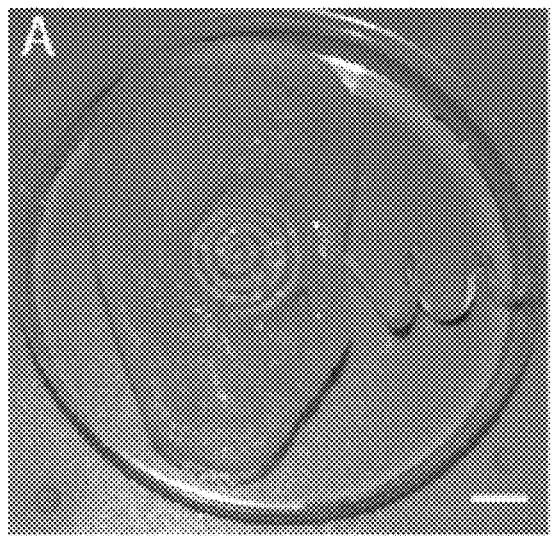
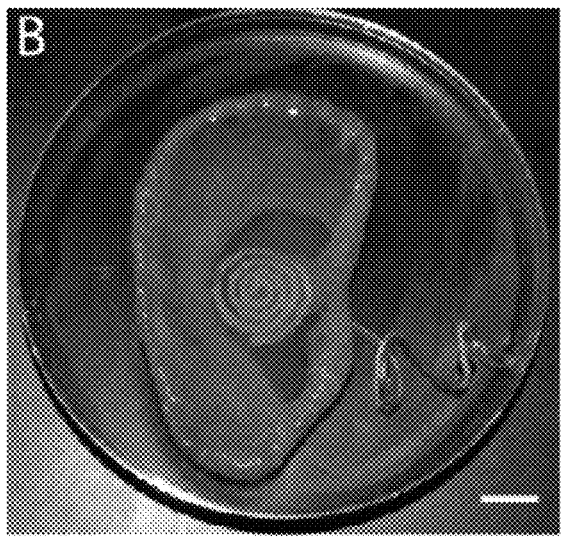
Figure 2a
Figure 2b
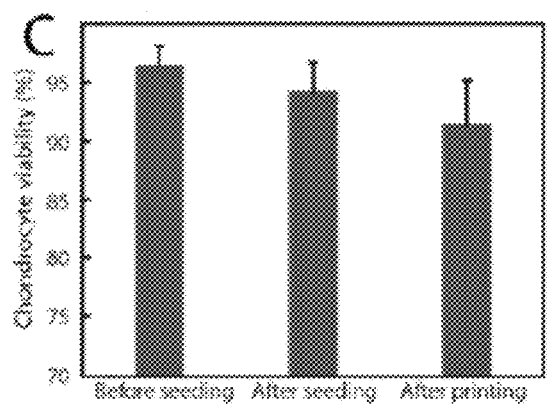
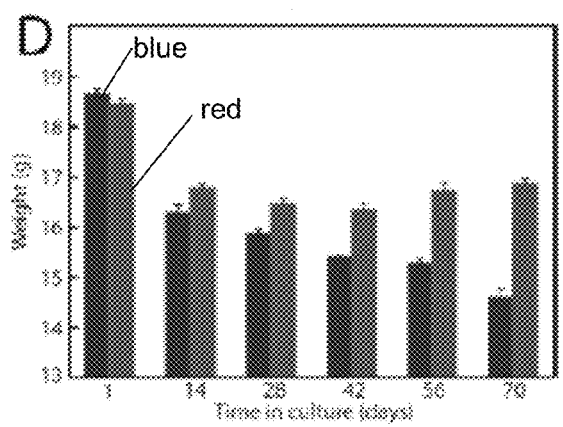
Figure 2c
Figure 2d

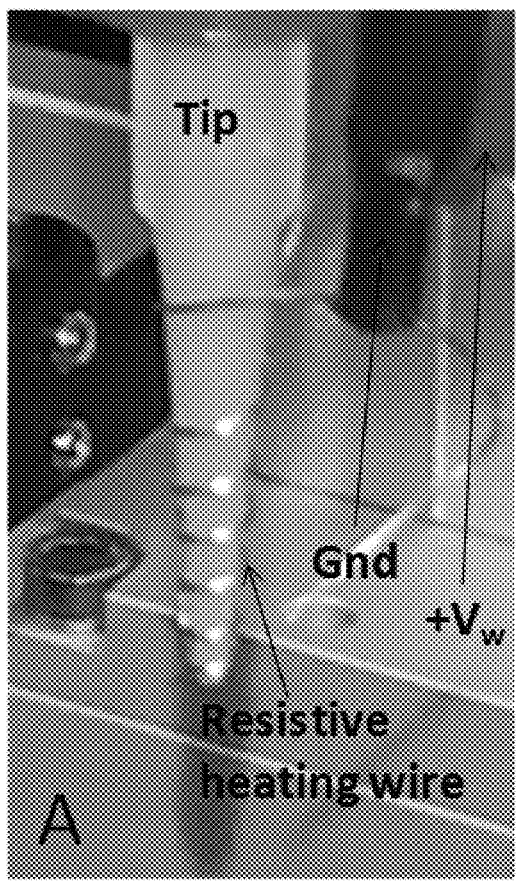 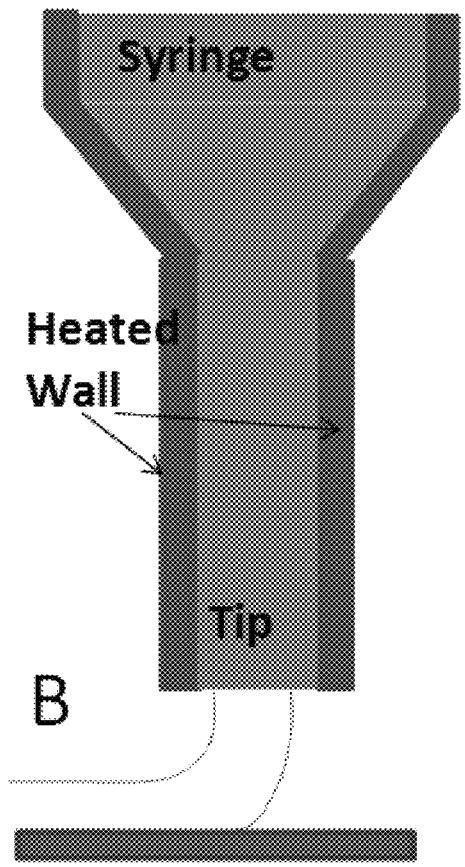
Figure 8a                    Figure 8b

MULTI-FUNCTIONAL HYBRID DEVICES/STRUCTURES USING 3D PRINTING

CROSS-REFERENCE TO PRIOR FILED APPLICATIONS

This application claims priority to U.S. provisional application 61/774,913 which was filed on Mar. 8, 2013 which is incorporated herein in its entirety.

TECHNICAL FIELD

This invention relates generally to 3D printing of nanoelectronic materials and in more particular interweaving of electronic and biological functionality using 3D printing.

BACKGROUND

The design and implementation of bionic organs and devices that enhance human capabilities, known as cybernetics, has been an area of increasing scientific interest. This field has the potential to generate customized replacement parts for the human body, or even create organs containing capabilities beyond what human biology ordinarily provides. In particular, the development of approaches for the direct multidimensional integration of functional electronic components with biological tissue and organs could have tremendous impact in regenerative medicine, prosthetics, and human-machine interfaces. Recently, several reports have described the coupling of electronics and tissues using flexible and/or stretchable planar devices and sensors that conform to tissue surfaces, enabling applications such as biochemical sensing and probing of electrical activities on surfaces of the heart, lungs, brain, skin, and teeth. However, attaining seamless three dimensionally (3D) entwined electronic components with biological tissues and organs is significantly more challenging. Tissue engineering is guided by the principle that a variety of cell types can be coaxed into synthesizing new tissue if they are seeded onto an appropriate three-dimensional hydrogel scaffold within an accordant growth environment. Following in vivo or in vitro culture, tissue structures form which possess the morphology of the original scaffold. A major challenge in traditional tissue engineering approaches is the generation of cell-seeded implants with structures that mimic native tissue, both in anatomic geometries and intratissue cellular distributions. Techniques such as seeding cells into nonadhesive molds or self-folding scaffolds have been used to fabricate three-dimensional tissue constructs with complex 3D geometries. Yet, existing techniques are still incapable of easily creating organ or tissue parts with the required spatial heterogeneities and accurate anatomical geometries to meet the shortage of donor organs for transplantation. For instance, total external ear reconstruction with autogenous cartilage with the goal of recreating an ear that is similar in appearance to the contralateral auricle remains one of the most difficult problems in the field of plastic and reconstructive surgery.

Additive manufacturing techniques such as 3D printing offer a potential solution via the ability to rapidly create computer-aided design (CAD) models by slicing them into layers and building the layers upward using biological cells as inks in the precise anatomic geometries of human organs. Variations of 3D printing have been used as methods of solid freeform fabrication, although its use has mainly been limited to the creation of passive mechanical parts. Extrusion-based 3D printing has been used to engineer hard tissue scaffolds such as knee menisci and intervertebral discs complete with encapsulated cells. This technique offers the ability to create spatially heterogeneous multi-material structures by utilizing deposition tools that can extrude a wide range of materials. Further, nanoscale functional building blocks enable versatile bottom-up assembly of macroscale components possessing tunable functionalities. This could allow for the simultaneous printing of nanoelectronic materials and biological cells to yield three dimensionally integrated cyborg tissues and organs exhibiting unique capabilities.

SUMMARY OF THE INVENTION

A bioelectronic device and method of making is disclosed. The device includes a scaffold formed via 3D printing. The device also includes a biologic and an electronic device formed via 3D printing, the biologic and electronic device being interweaved with or coupled to the scaffold. The electronic component may e.g., include at least one of hard conductors, soft conductors, insulators and semiconductors. The scaffold may be formed of at least one of synthetic polymers and natural biological polymers. The biologic may include at least one of animal cells, plant cells, cellular organelles, proteins and DNA (including RNA).

Synthetic polymers may include e.g., at least one of silicone and poly-lactic-co-glycolic acid. Natural biological polymers may e.g., include at least one of a polysaccharide and an integrated protein. Polysaccharides may e.g., include alginate, DNA polymers, chitosan, and hyaluronan. Integrated proteins may e.g., include collagen or fibrin. Animal cells may include e.g., chrondrocytes and glial cells. Cellular organelles may include e.g. thylakoids.

The electronic component may be formed of laser-curable materials. The electronic component may be is formed from a polymer. The electronic component may be formed from nano or micro-scale integrated electronic components. The electronic component may be formed of at least one of a conductor, semiconductor, and/or insulating material. Suitable polymers may e.g., include poly(3,4-ethylenedioxythiophene), poly(styrenesulfonate), PEDOT-PSS. Nano or micro-scale integrated electronic components may e.g., include conductive and semiconductive micro and nanoparticles.

The scaffold may generally be formed into the shape of an external animal anatomical feature (e.g., an ear or nose). The scaffold may generally be formed into the shape of internal animal or plant anatomical conduit (e.g. vasculature). The scaffold may generally be formed into the shape of plant structure (e.g., a leaf, flower, or plant). The electronic component may be formed of a variety of materials including e.g., silver nanoparticle infused silicone, liquid metals, and conducting polymers. Structural components (e.g. silicone) may be organized into coil and/or woven grid structures, as well as other device designs such as electrodes and interdigitated electrodes.

The electronic component may have electronic material properties that are modulated during printing via Peltier-based stage heating. The scaffold may have structural and geometric features that are reduced to micron-scale via application of resistive heating of material syringes and extrusion tips. The scaffold may be cured via heat or light (e.g. Peltier, extruder and tip heat exchangers, and lasers). The electronic component may be a semiconductor device such as a light emitting diode or a light harvesting structure formed via 3D printing (e.g., bionic leaf).

The electronic device may include an integrated seeded matrix and insulating material and embedded nano-scale conductive components (e.g., bionic ear). The electronic device may include hydrogel-based conductive elements arranged into active capacitive components (e.g., a conductive hydrogel actuator and sensor). The electronic device may include a piezoelectric element (e.g., actuators, sensors, and printed robotics).

A method of forming a bioelectronic device is also disclosed. The method includes forming a scaffold via 3D printing and forming a biologic and an electronic device via 3D printing, the biologic and an electronic device being interweaved with or coupled to the scaffold.

BRIEF DESCRIPTION OF THE FIGURES

FIG. 1b is a diagram showing images of the functional materials, including biological (chondrocytes), structural (silicone), and electronic (AgNP infused silicone) and a 3D printer used for the printing process used to form the bionic ear of FIG. 1a;

FIG. 2a is a image of the 3D printed bionic ear immediately after printing (scale bars are 1 cm);

FIG. 2b is the 3D printed bionic ear during in vitro culture (scale bars are 1 cm);

FIG. 2c is a graph of the chondrocyte viability at various stages of the printing process (error bars show standard deviation with N=3);

FIG. 2d is a graph of the variation in the weight of the printed ear over time in culture, where the ear includes chondrocyte-seeded alginate (red) or only alginate (blue) (error bars show standard deviation with N=3);

FIG. 4a is an image of the experimental setup used to characterize the bionic ear. The ear is exposed to a signal from a transmitting loop antenna. The output signal is collected via connections to two electrodes on the cochlea. Scale bar is 1 cm;

FIG. 4b is a graph showing the response of the bionic ear to radio frequencies in terms of S21, the forward power transmission coefficient;

FIG. 8a is a photograph of resistively heated tip for heated extrusion of fine features via 3D printing;

FIG. 8b is a schematic diagram showing heat exchange principle where walls become constant temperature heaters for modulation of fluid flow via rheological property tuning;

DETAILED DESCRIPTION

Disclosed herein are conceptually new approaches that address the aforementioned challenges by fully interweaving functional electronic components with biological tissue via 3D printing of nanoelectronic materials and viable cell-seeded hydrogels in the precise anatomic geometries of human organs. Since electronic circuitry is at the core of sensory and information processing devices, in vitro culturing of the printed hybrid architecture enables the growth of "cyborg organs" exhibiting enhanced functionalities over human biology. The disclosed approaches offer the ability to define and create spatially heterogeneous constructs by extruding a wide range of materials in a layer-by-layer process until the final stereolithographic geometry is complete. The concept of 3D printing living cells together with electronic components and growing them into functional organs represents a new direction in merging electronics with biological systems. Indeed, such cyborg organs are distinct from either engineered tissue or conformal planar/flexible electronics and offer a unique way of attaining a three-dimensional merger of electronics with tissue.

Figure 1A:
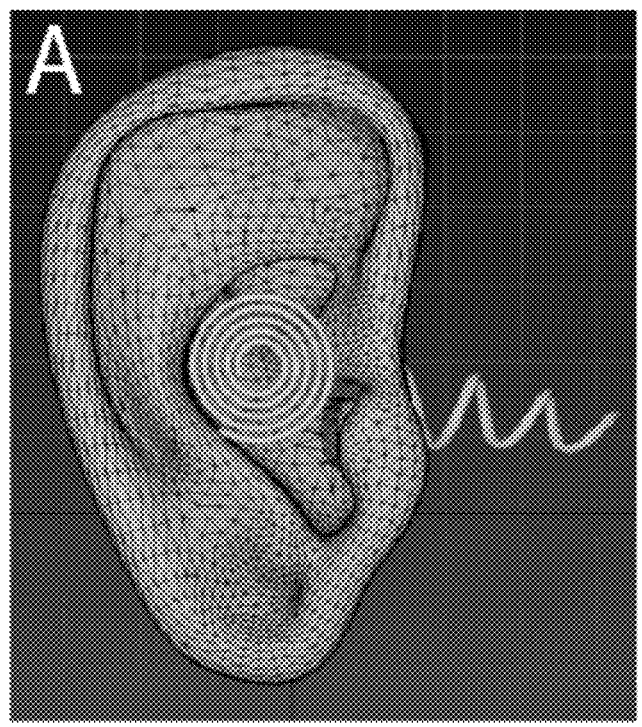
FIG. 1a is a block diagram showing a CAD drawing of a bionic ear.

As a proof of concept of this approach, 3D printing was used to create a viable ear auricle that also contains electronics that enable alternative capabilities to human hearing. Human organs comprising predominantly of cartilaginous tissue, such as the ear auricle, represent suitable prototype candidates to investigate the feasibility of our approach. This is due to (1) the inherent complexity in the ear's anatomical geometry, which renders it difficult to bioengineer via traditional tissue engineering approaches as well as (2) the simplicity in its cartilage tissue level structure due to the lack of vasculature. Additionally, bottom-up assembly of nanoelectronic matrices provides the ability to hierarchically generate functional macroscale electronic components. Specifically, 3D printing was used to create a chondrocyte-seeded alginate hydrogel matrix with an electrically conductive silver nanoparticle (AgNP) infused inductive coil antenna, connecting to cochlea-shaped electrodes supported on silicone. Taken together, the result is three-dimensional integration of functional electronic components within the complex and precise anatomic geometry of a human ear (FIG. 1).

Figure 1B:
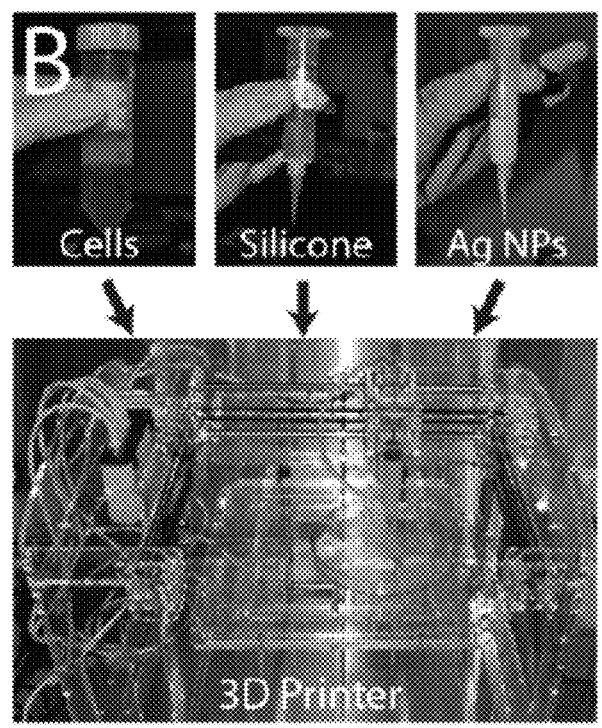
Figure 1C:
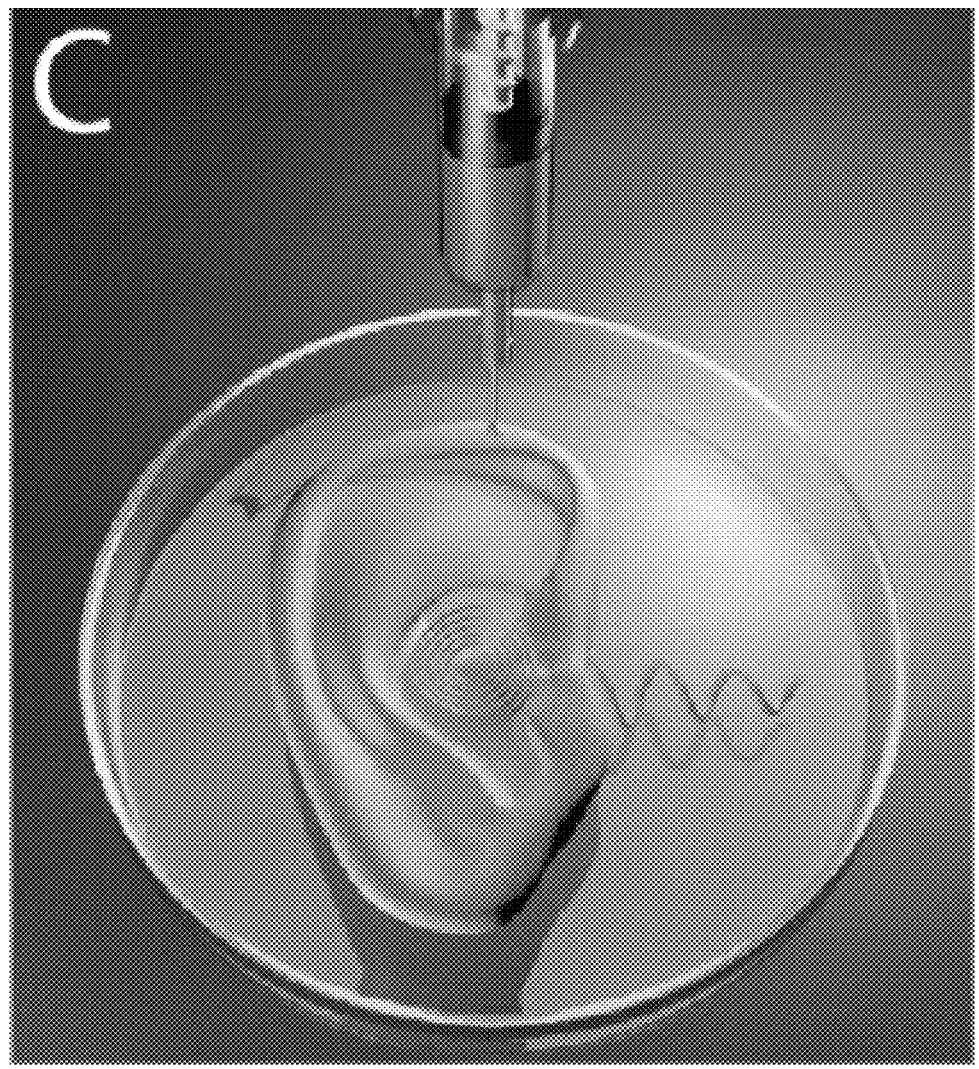
FIG. 1c is an illustration of a 3D printed bionic ear.

The following steps are involved in the process. First, a CAD drawing of the bionic ear (FIG. 1a) is used to prescribe the anatomic geometry and the spatial heterogeneity of the various functional materials. As described above, three materials comprise the three functional constituents (structural, biological, and electronic) of the bionic ear. These materials are fed into a syringe extrusion based Fab@Home 3D printer (The NextFab Store, Albuquerque, N. Mex.) (FIG. 1b). The printed bioelectronic hybrid ear construct is then cultured in vitro to enable cartilage tissue growth to form a cyborg ear with the capability of sensing electromagnetic signals in the radio frequency (RF) range by means of an inductive coil acting as a receiving antenna (FIG. 1c).

In this example, the bionic ear was constructed as follows. For the scaffold, an alginate hydrogel matrix with viable chondrocytes was preseeded at a density of ~60 million cells/mL. Additional information is available in Mannoor et al., "3D Printed Bionic Ears" Nano Lett., 2013, 13 (6), pp 2634-2639 and the associated Supporting Information which are incorporated herein in their entirety. Alginate matrix is three dimensionally stable in culture, nontoxic, preseeding, and extrusion compatible, and a suitable cell delivery vehicle because cross-linking can be initiated prior to deposition. Chondrocytes used for the printing were isolated from the articular cartilage of one month old calves (Astarte Biologics, Redmond, Wash.). A CAD drawing of a human ear auricle in stereolithography format (STL) with an integrated circular coil antenna connected to cochlea-shaped electrodes was used to define the print paths by slicing the model into layers of contour and raster fill paths. Cross-linking was initiated in the alginate hydrogel matrix pre-seeded with viable chondrocytes, which was then 3D printed along with conducting (AgNP infused) and nonconducting silicone solutions (Supporting Information Movie 1). Together, this method produced the biological, electronic, and structural components of the bionic organ in a single process.

Figure 2E:
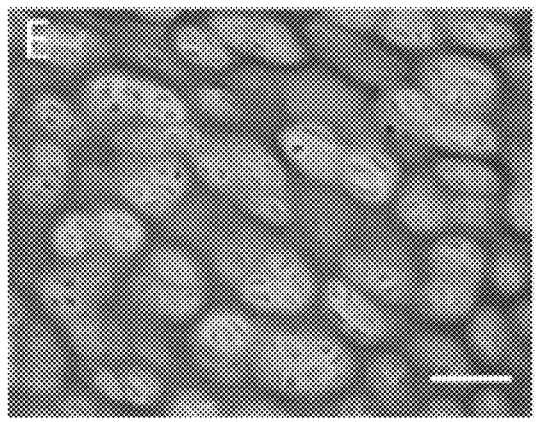
FIG. 2e is a histologic evaluation of chondrocyte morphology using H&E staining.

FIG. 2a shows the 3D printed bionic ear immediately after printing. Notably, it is found to faithfully reproduce the CAD drawing, in the precise spatiality for each material as dictated by the design. The printed ear construct was immersed in chondrocyte culture media containing 10 or 20% fetal bovine serum (FBS), which was refreshed every 1-2 days (see Supporting Information). The hybrid ear showed good structural integrity and shape retention under culture (FIG. 2b). Over time, the construct gradually became more opaque; this was most apparent after four weeks of culture and is grossly consistent with developing an extracellular matrix (ECM). The gross morphology of the bionic ear after 10 weeks of in vitro culture is shown in the Supporting Information.

Viability was tested immediately before and during the various stages of the printing process. Initial viability of cells was determined after culturing using a Trypan blue cell exclusion assay (Corning Cellgrow, Mediatech, Va.) and was found to be 96.4±1.7% (FIG. 2C) (see Supporting Information). The printed cell-seeded alginate ear was also tested with a LIVE/DEAD Viability Assay (Molecular Probes, Eugene, Oreg.) and exhibited a cell viability of 91.3±3.9% with homogeneous chondrocyte distribution. This result suggests that the printing process, including cell encapsulation and deposition, does not appreciably impact chondrocyte viability.

Notably, this approach of printing a preseeded hydrogel matrix eliminates the major problems associated with seeding depth limitations and nonuniform seeding in traditional methods for seeding premolded 3D scaffolds. Seeding chondrocytes into a bioabsorbable alginate matrix and shaping it via 3D printing localizes the cells to a desired geometry, allowing for new ECM production in defined locations when cultured in nutritive media. As tissue develops, the polymer scaffold is reabsorbed (FIG. 2D), so that the new tissue retains the shape of the polymer in which the cells were seeded. The biodegradable scaffolding provides each cell with better access to nutrients and more efficient waste removal.

Figure 2F:
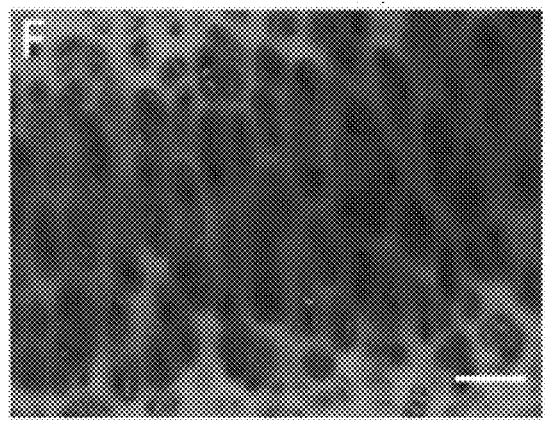
FIG. 2f is a safranin O staining of the neocartilaginous tissue after 10 weeks of culture.
Figure 2G:
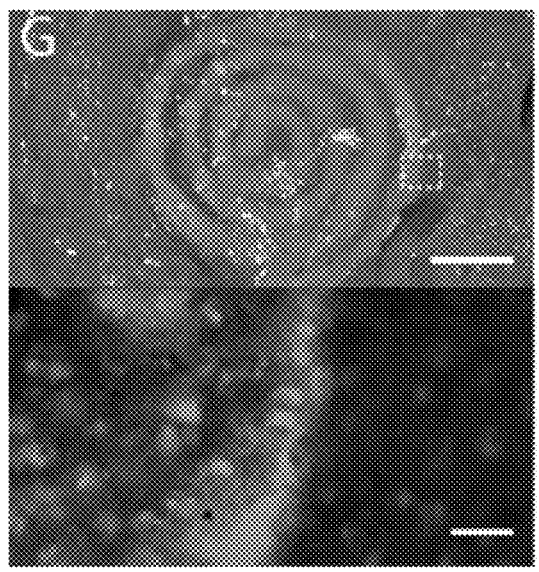
FIG. 2g is a photograph (top) and fluorescent (bottom) image showing viability of the neocartilaginous tissue in contact with the coil antenna.
Figure 2H:
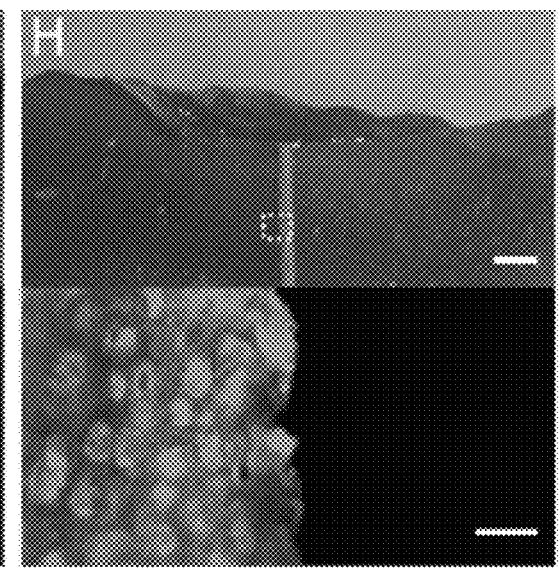
FIG. 2h is a photograph (top) and fluorescent (bottom) image of a cross section of the bionic ear showing viability of the internal cartilaginous tissue in contact with the electrode (top scale bars are 5 mm, bottom are 50 µm).

Next, histologic evaluation was used to compare the morphology of chondrocytes in the neocartilage of the bionic ear to that of the native cartilaginous tissue. Hematoxylin and eosin (H&E) staining revealed uniform distribution of the chondrocytes in the constructs (FIG. 2E) (see Supporting Information). Histology of the ear tissue with Safranin O staining indicated relatively uniform accumulation of proteoglycans in the cultured ear tissue (FIG. 2F). These biochemical data are consistent with the development of new cartilage. Finally, fluorescent measurements were used to ascertain the viability of the 3D printed bionic ear tissue after 10 weeks of in vitro growth culture using fluorescein diacetate (FDA) and propidium iodide (PI) stains. FIGS. 2G and 2H show the tissue covering the coil antenna and the internal tissue that is in contact with the electrode that runs perpendicular through the tissue, respectively. In both cases, the grown cartilage exhibited excellent morphology and tissue level viability. Notably, this approach of culturing tissue in the presence of abiotic electronic materials could minimize the immune response of the grown tissue.

Figure 3A:
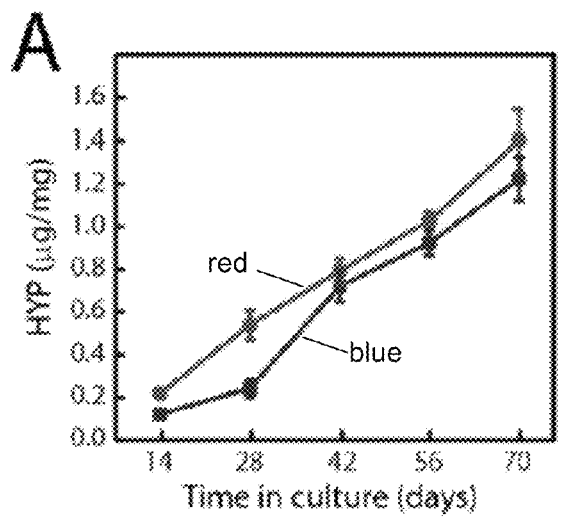
FIG. 3a is a graph showing variation of HYP content over time in culture with 20% (red) and 10% (blue) FBS (error bars show standard deviation with N=3)
Figure 3B:
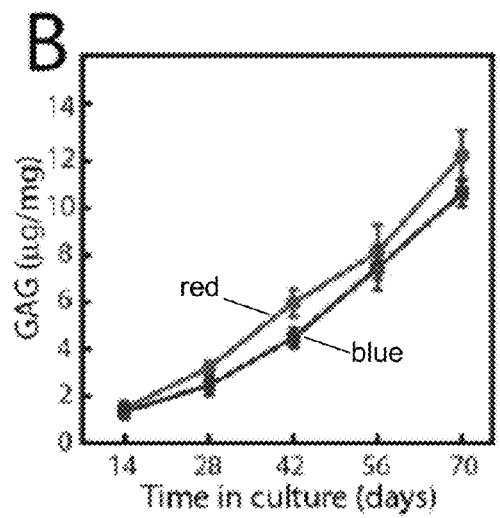
FIG. 3b is a graph showing variation of GAG content over time in culture with 20% (red) and 10% (blue) FBS (error bars show standard deviation with N=3).

The mechanical properties of the cartilage were characterized at various stages of growth, as ECM development correlates strongly with the developing tissue's mechanical properties. First, extensive biochemical and histologic characterizations were performed. Samples were removed from cultures containing 10 and 20% FBS at 2, 4, 6, 8, and 10 weeks and frozen to measure DNA content of the neocartilage and for biochemical evaluation of the ECM (see Supporting Information). ECM accumulation in the constructs was evaluated by quantifying the amount of two important components of ECM: (1) hydroxyproline (HYP) as a marker of collagen content and (2) sulfated glycosaminoglycan (GAG) as a marker of proteoglycans. By week 10, the HYP content increased to 1.2±0.1 and 1.4±0.2 µg/mg for cultures containing 10 and 20% FBS, respectively (FIG. 3A). The corresponding values of GAG content for week 10 were 10.6±0.6 and 12.2±1.0 µg/mg (FIG. 3B). This increase in GAG and HYP content indicates that chondrocytes are alive and metabolically active in culture.

Figure 3C:
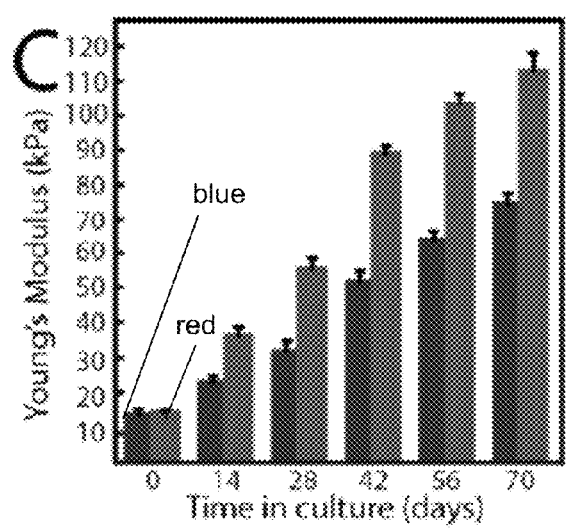
FIG. 3c is a graph showing variation of Young's modulus of 3D printed dog bone constructs over time in culture with 20 million (blue) and 60 million (red) cells/mL (error bars show standard deviation with N=3).
Figure 3D:
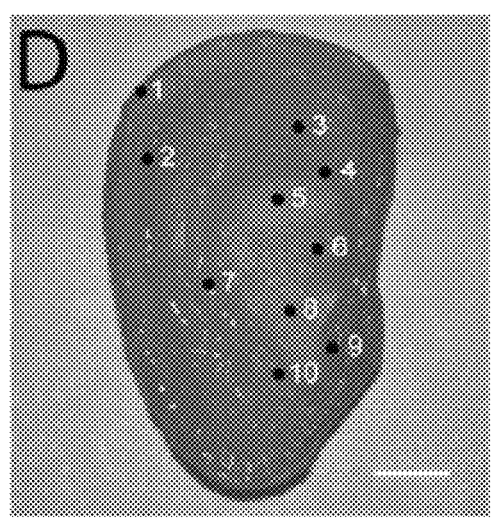
FIG. 3d is a photo showing various anatomic sites of the ear auricle, with corresponding hardness listed in Table 1 (Scale bar is 1 cm)

Next, tensile properties were analyzed by testing 3D printed chondrocyte-alginate dogbone samples at various points in culture in which the dogbones contained the same cell densities and identical culturing conditions as the ear (see Supporting Information). Evaluation of the mechanical properties indicated that the Young's modulus of the dogbones increased with time from 14.16 to 111.46 kPa at week 10 (FIG. 3C). Dogbones of a lower chondrocyte density of 20 million cells/mL were also tested under similar conditions to understand the effect of the initial chondrocyte density in the mechanical properties of the grown tissue. These were found to possess a lower Young's modulus of 73.26 kPa at week 10. Next, the hardness of the grown cartilaginous tissue of the 3D printed auricle was characterized using nanoindentation measurements. The indentations were performed at the various anatomic sites of the auricle (FIG. 3D). As shown in Table 1, these hardness values were found to be relatively uniform, ranging from 38.50 to 46.80 kPa, confirming the structural integrity of the printed ear.

TABLE 1

| Part | Mean Hardness (kPa) |
| --- | --- |
| 1. Helix | 44.85 ± 2.68 |
| 2. Scapha | 38.93 ± 3.00 |
| 3. Fossa | 42.40 ± 2.87 |
| 4. Crura Antihelix | 45.47 ± 3.95 |
| 5. Cymba Conchae | 41.53 ± 4.36 |
| 6. Crus of Helix | 46.80 ± 4.72 |
| 7. Antihelix | 40.67 ± 3.13 |
| 8. Cavum Conchae | 38.50 ± 1.73 |
| 9. Tragus | 40.10 ± 2.42 |
| 10. Antitragus | 39.27 ± 3.26 |

To demonstrate the enhanced functionalities of the 3D printed bionic ear, we performed a series of electrical characterizations. First, the resistivity of the coil antenna was measured using four point probe measurements and found to be dependent on the volumetric flow rate used for printing the conducting AgNP-infused silicone (see Supporting Information). At the optimum flow rate, the resistivity of the printed coil was found to be $1.31 \times 10^{-6}$ Ω·m, which is only 2 orders of magnitude higher than pure silver ($1.59 \times 10^{-8}$ Ω·m). Next, we performed wireless radio frequency reception experiments. To demonstrate the ability of the bionic ear to receive signals beyond normal audible signal frequencies (in humans, 20 Hz to 20 kHz), we formed external connections to the cochlea-shaped electrodes stemming from the inductive coil of the bionic ear (FIG. 4A). The ear was then exposed to sine waves of frequencies ranging from 1 MHz to 5 GHz. The S21 (forward transmission coefficient) parameter of the coil antenna was analyzed using a network analyzer and was found to transmit signals across this extended frequency spectrum (FIG. 4B).

Figure 4C:
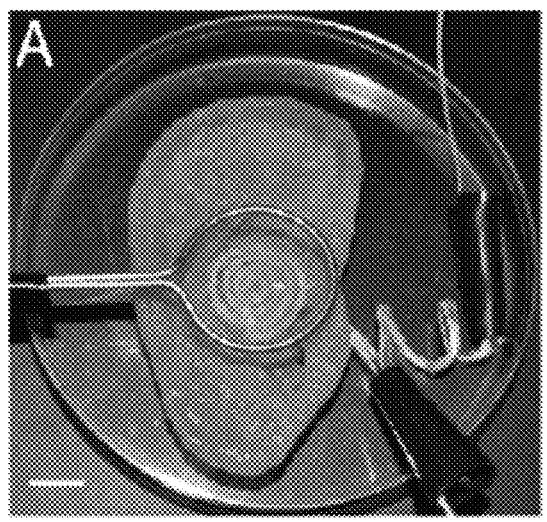
FIG. 4c is a schematic representation of the radio signal reception of two complementary (left and right) bionic ears.
Figure 4C:
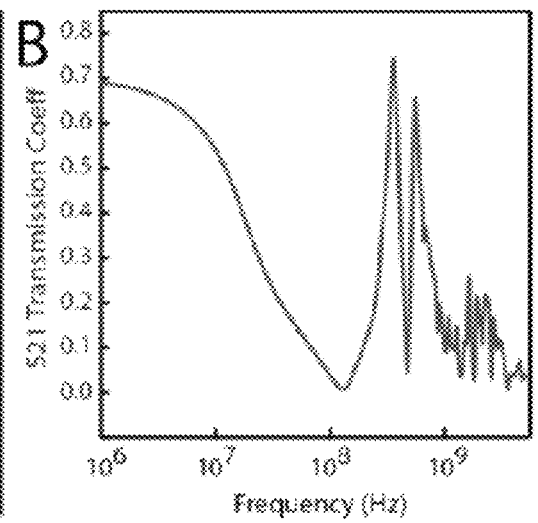
Figure 4C:
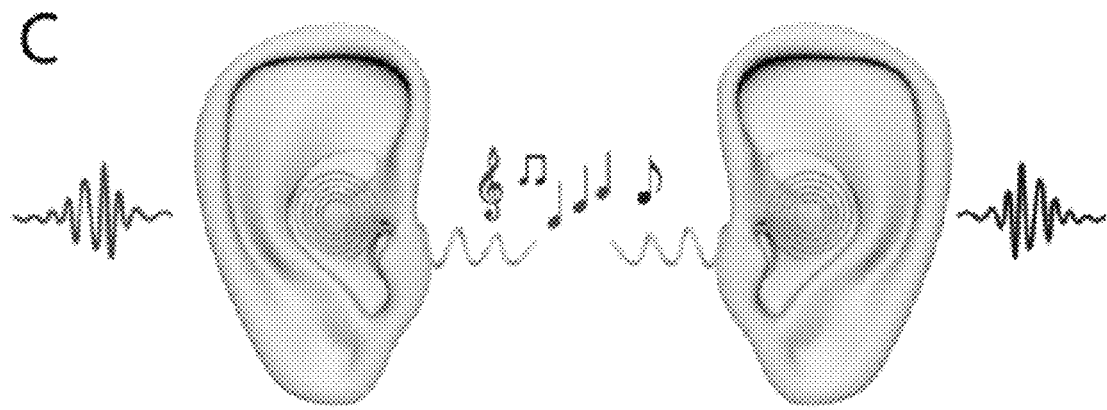
Figure 4D:
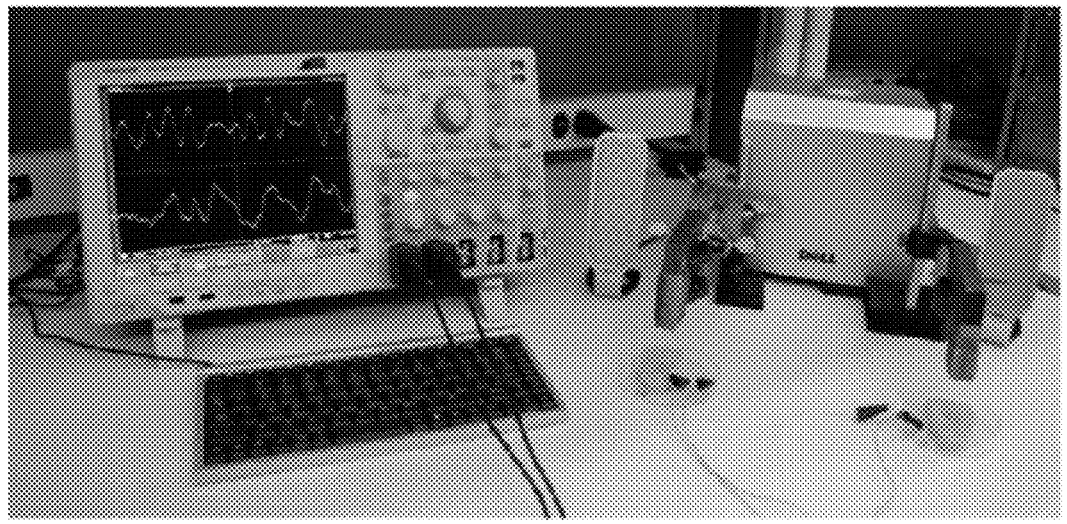
FIG. 4d is a photograph of complementary bionic ears listening to stereophonic audio music (see Supporting Information Movie 2)
Figures 4E, 4F:
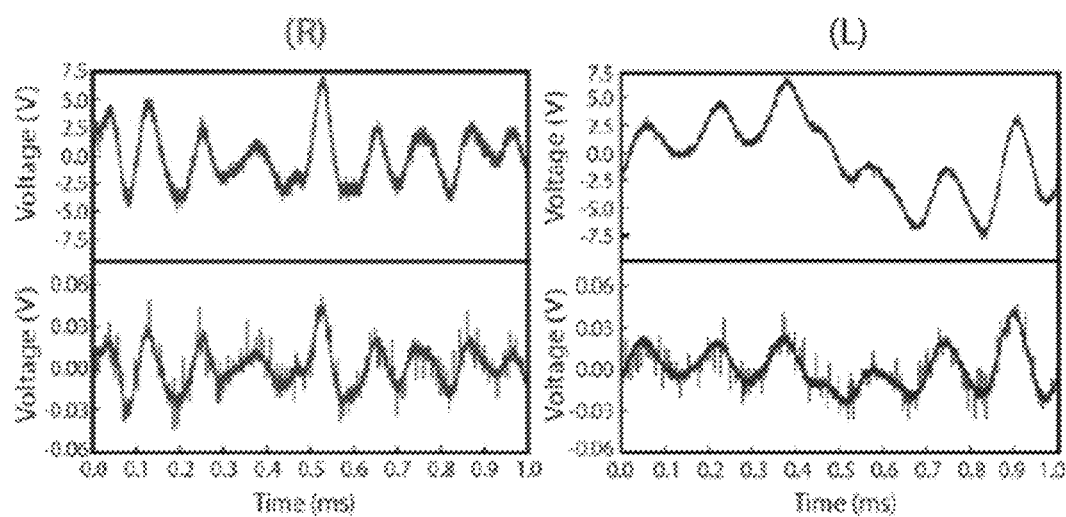
FIGS. 4e and 4f are graphs showing the transmitted (top) and received (bottom) audio signals of the right (R) and left (L) bionic ears.

Most importantly, as a demonstrative example of the versatility in modifying the final organ by modifying the CAD design, we printed a complementary left ear by simply reflecting the original model (see Supporting Information). Left and right channels of stereophonic audio were exposed to the left and right bionic ear via transmitting magnetic loop antennas with ferrite cores (FIG. 4C). The signals received by the bionic ears were collected from the signal output of the dual cochlea shaped electrodes and fed into a digital oscilloscope and played back by a loud speaker for auditory and visual monitoring. Excerpts of the transmitted and received signals of duration 1 ms for both the right and left bionic ears are shown in FIG. 4D and are found to exhibit excellent reproduction of the audio signal. Significantly, the played back music (Beethoven's "Für Elise") from the signal received by the bionic ears possessed good sound quality (Supporting Information Movie 2).

Heated Extrusion and Thermal Curing Functionality

Figure 5A:
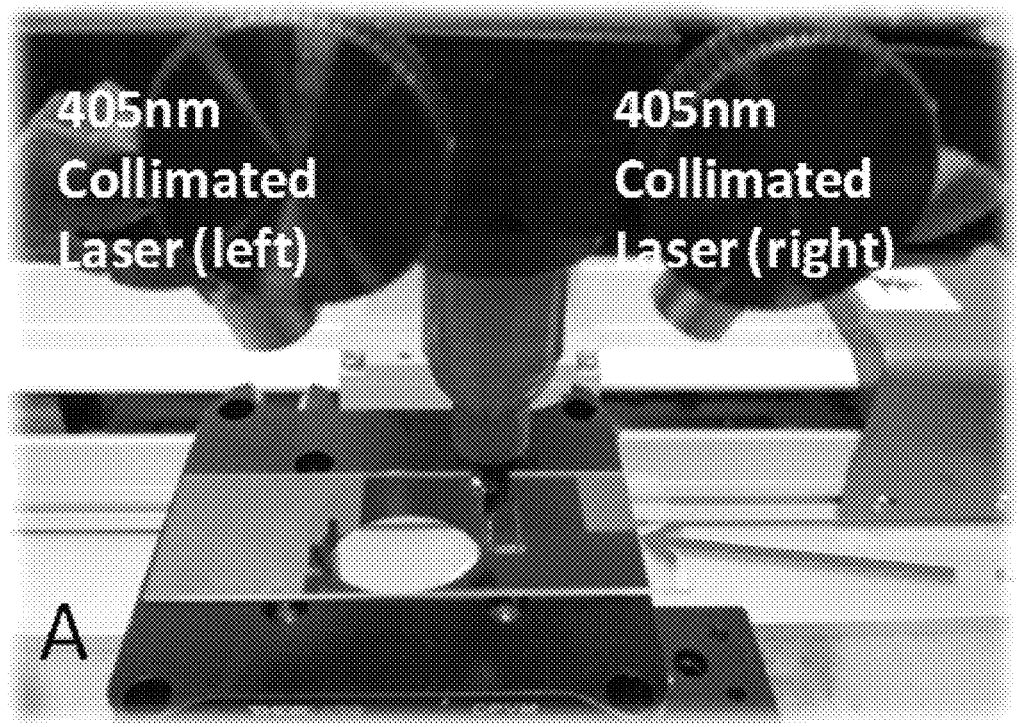
FIG. 5a is a picture showing UV-ink that has been cured by 2 aligned UV lasers immediately after extruded from its uncured state.
Figure 5B:
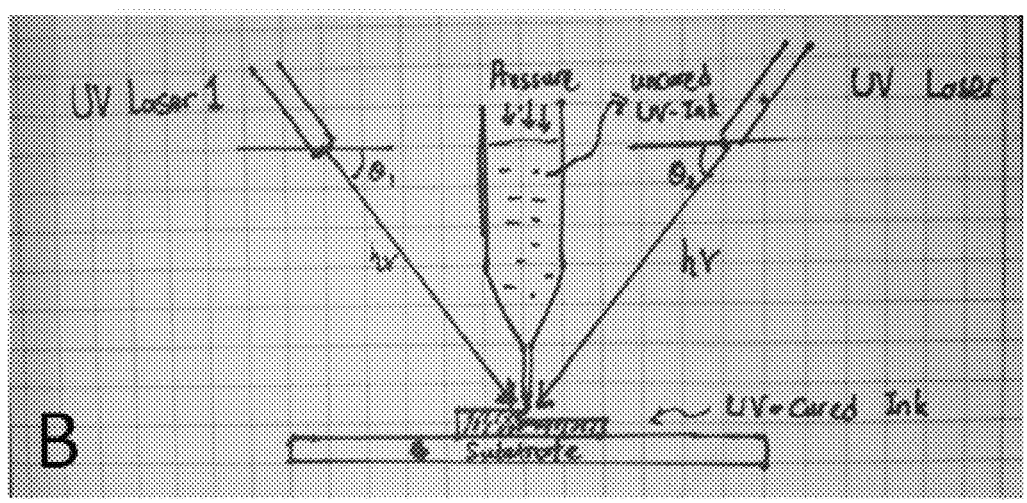
FIG. 5b is a diagram schematic showing calibration of the set up to align the collimated laser system to cure the uncured UV-Ink once it has been extruded from the print head to form a 3 dimensional structure.

In order to facilitate the curing process, Ultraviolet curable ink (UV-ink) may be used and may be laser cured. FIG. 5a is a picture showing UV-ink that has been cured by 2 aligned UV lasers immediately after extruded from its uncured state. Blue arrow shows printed LTV Ink that has been cured with laser. FIG. 5b is a diagram schematic showing calibration of the set up to align the collimated laser system to cure the uncured UV-Ink once it has been extruded from the print head to form a 3 dimensional structure.

Figure 6A:
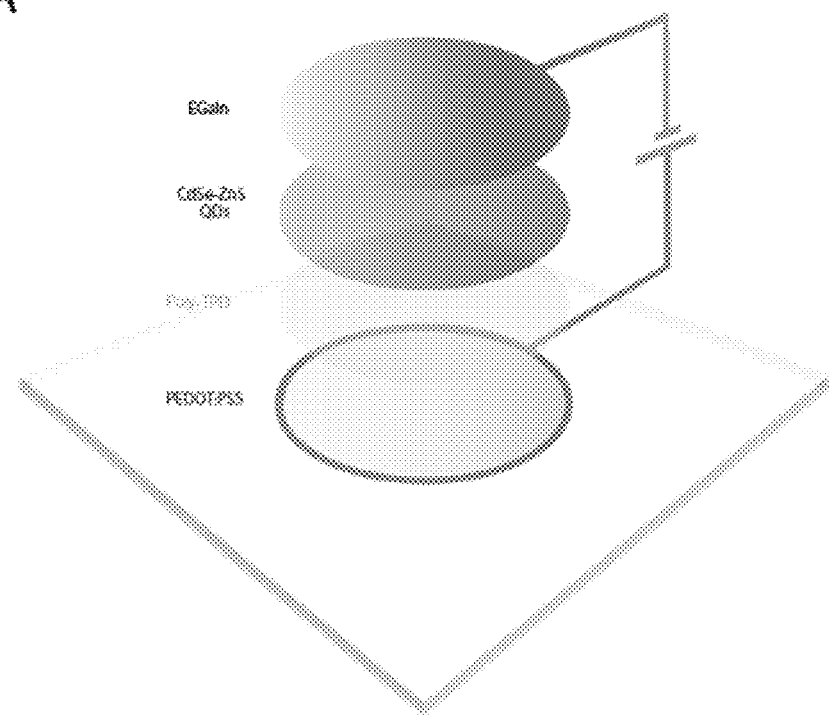
FIG. 6a is a schematic diagram of an LED design, with PEDOT:PSS on top of UV cured transparent substrate that has been printed with the LTV system.
Figure 6B:
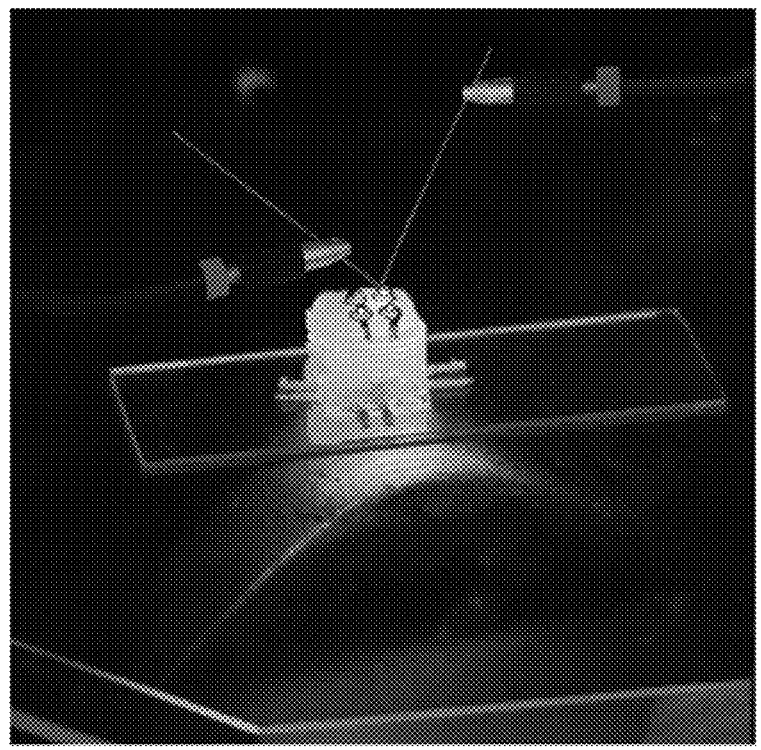
FIG. 6b is a photograph showing an LED Printed on UV cured adhesive on top of Silicone Rubber Matrix that glows and the light diffuses into the silicone.

Devices may be formed with a wide variety of integrated electronic functionality. Laser curing was implemented in fabrication of a 3D light-emitting diode. Laser curing was used to cure thin-film conductive components of the device. In addition to potential implementation of optical functionality to the bionic ear using these principles, one could also apply the laser curing for optimized design of the bionic ear electronic transducer which was made via conductive nanoparticles embedded in printable insulating material (silicone). It should be understood that these techniques may be used to fabricate a variety of devices. FIG. 6a is a schematic diagram of an LED design, with PEDOT:PSS on top of UV cured transparent substrate that has been printed with the LTV system. The layers PEDOT:PSS, Poly-TPD were annealed at 150 degree Celsius and 110 degree Celsius respectively with the Peltier heating system. FIG. 6b is a photograph showing an LED Printed on UV cured adhesive on top of Silicone Rubber Matrix that glows and the light diffuses into the silicone.

Figure 7A:
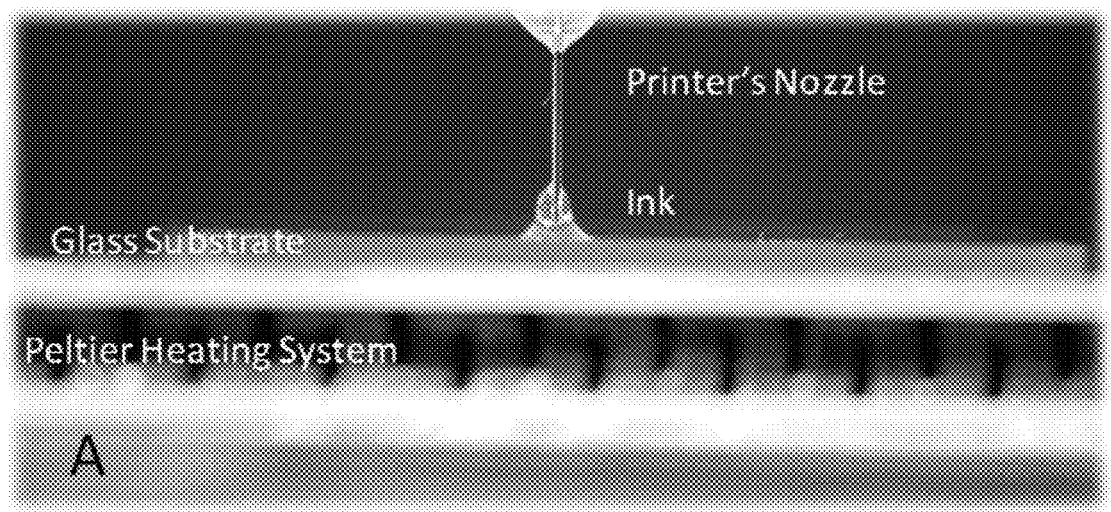
FIG. 7a is a schematic diagram of a thermo-electric or Peltier substrate heating system.
Figure 7B:
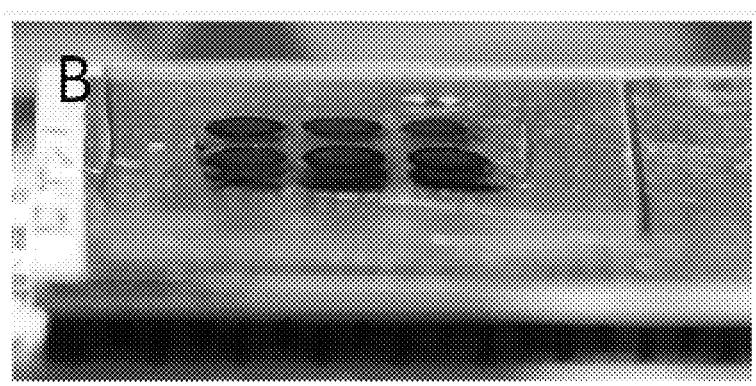
FIG. 7b is a photograph showing a annealing of the Printed Films as part of the device fabrication.
Figure 7C:
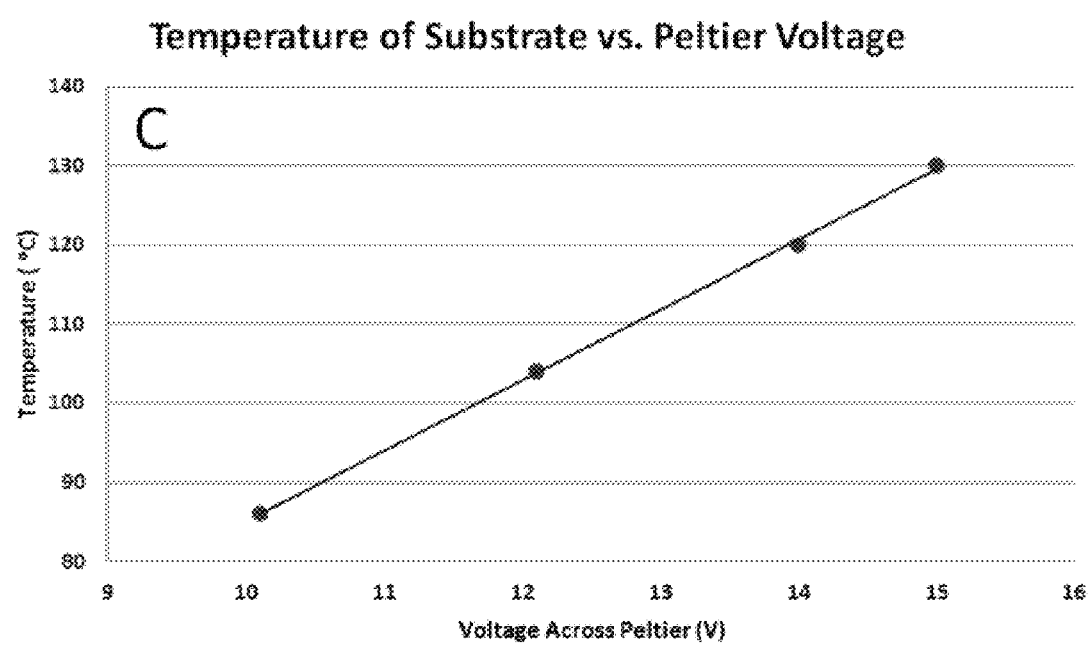
FIG. 7c is a graph showing that the temperature of the substrate is controlled by changing the voltage applied to the Peltier heating system.

Precise temperature control of the substrate may be used to facilitate the process. Heated extrusion and thermal curing principle was implemented in fabrication of 3D printed thin-wall conduits made of both alginate and silicone biocompatible materials. In those examples, devices could not be extruded when the feature size (determined by syringe diameter) is less than ~200 µm. These conduits may be used in a variety of devices including the bionic ear. These techniques may also be useful in construction of other structures. FIG. 7a is a schematic diagram of a thermoelectric or Peltier heating system. Using this structure, the substrate temperature can be change during printing to control film formation. FIG. 7b is a photograph showing a annealing of the Printed Films as part of the device fabrication. FIG. 7c is a graph showing that the temperature of the substrate is controlled by changing the voltage applied to the Peltier heating system.

Figure 8C:
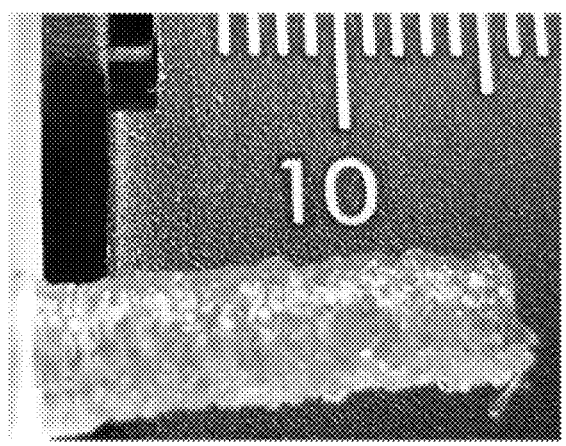
FIG. 8c is a photograph of thin walled cylindrical conduits of alginate.
Figure 8D:
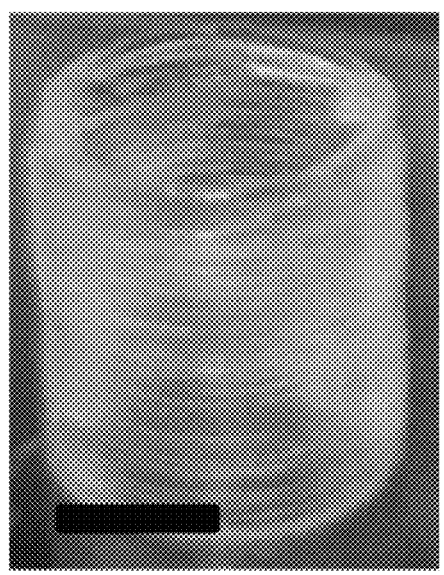
FIG. 8d is a photograph of thin walled cylindrical conduits of silicone.

FIG. 8a is a photograph of resistively heated tip for heated extrusion of fine features via 3D printing. FIG. 8b is a schematic diagram showing heat exchange principle where walls become constant temperature heaters for modulation of fluid flow via rheological property tuning. FIG. 8c is a photograph of thin walled cylindrical conduits of alginate. FIG. 8d is a photograph of thin walled cylindrical conduits of silicone (scale bar=1.5 mm) fabricated by the approach for potential integration to bionic ear device geometry or other devices with cylindrical feature functionality.

In summary, designer cyborg ears were fabricated that are capable of receiving electromagnetic signals over an expansive frequency range from hertz to gigahertz. Our strategy represents a proof of principle of intertwining the versatility of additive manufacturing techniques with nanoparticle assembly and tissue engineering concepts. The result is the generation of bona fide bionic organs in both form and function, as validated by tissue engineering benchmarks and electrical measurements. Such hybrids are distinct from either engineered tissue or planar/flexible electronics and offer a unique way of attaining a seamless integration of electronics with tissues to generate "off-the-shelf" cyborg organs. Finally, the use of 3D printing with other classes of nanoscale functional building blocks, including semiconductor, magnetic, plasmonic, and ferroelectric nanoparticles, could expand the opportunities for engineering bionic tissues and organs.

Bioelectronic, Self-Powering, and Microfluidic Functionalities

The 3D printed bionic leaf demonstrates the assembly of isolated cellular organelles, thylakoid photosynthetic functional units, with nano-scale electronics, graphene nanoribbon into a leaf-shaped hierarchical structure for bioelectric harvesting of sunlight. The following aspects were demonstrated:

1.) Incorporation of graphene nanoribbons (from AZ electronics research division);

2.) Testing of various ratios of PEDOT:PSS:graphene: thylakoid for optimal electron output;

3.) Measurement of the overall conversion efficiency of input light vs. output electrons;

4.) Incorporation of vasculature by printing sacrificial sugar networks 20 for water flow; and 5.) Process scaling to print multiple leaves which can be arranged into a tree architecture.

Functionality and Associated Bionic Principle

The leaf is a plant's photosynthetic organ, containing reaction centers for food energy production. The structure of a leaf is evolutionarily tailored to efficiently perform the various photosynthetic tasks such as: 1) light harvesting by the lens-like epidermal cells, 2) efficient light-harvesting and fast charge separation in the high surface area thylakoid cylindrical stacks (granum) in the chloroplast, and 3) the transport of water and photosynthates through the network of vascular bundles to and from chloroplasts, which are the organelles that perform photosynthesis within the mesophyll cells. The vascular bundle includes two channels, xylem and phloem, for conduction of the primary photosynthetic raw material (water) towards the chloroplasts, and carrying away outputs for storage and consumption, respectively.

Figure 9A:
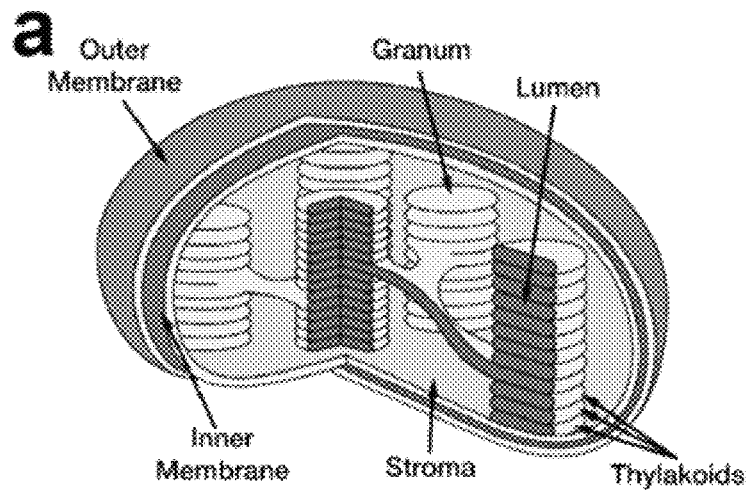
FIG. 9a is a block diagram of a chloroplast structure.
Figure 9B:
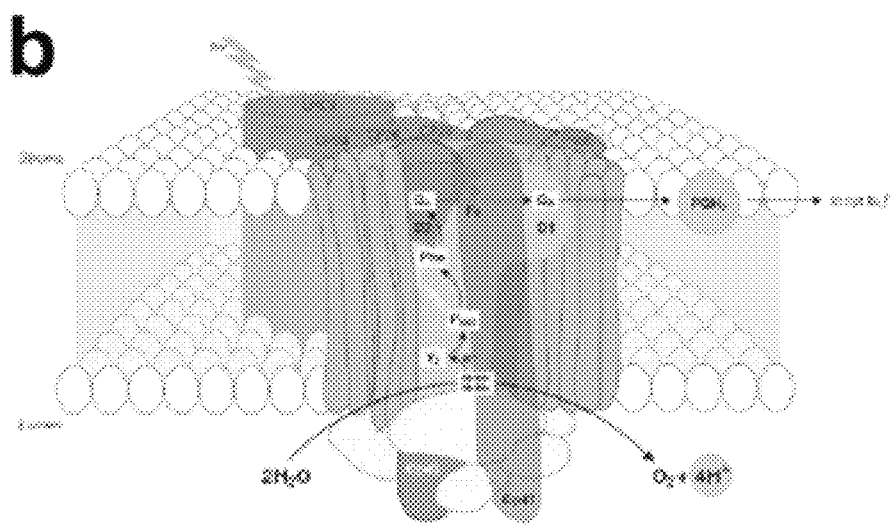
FIG. 9b is a block diagram of an organization of photosystem II and light-harvesting complex II in the thylakoid membrane.
Figure 9C:
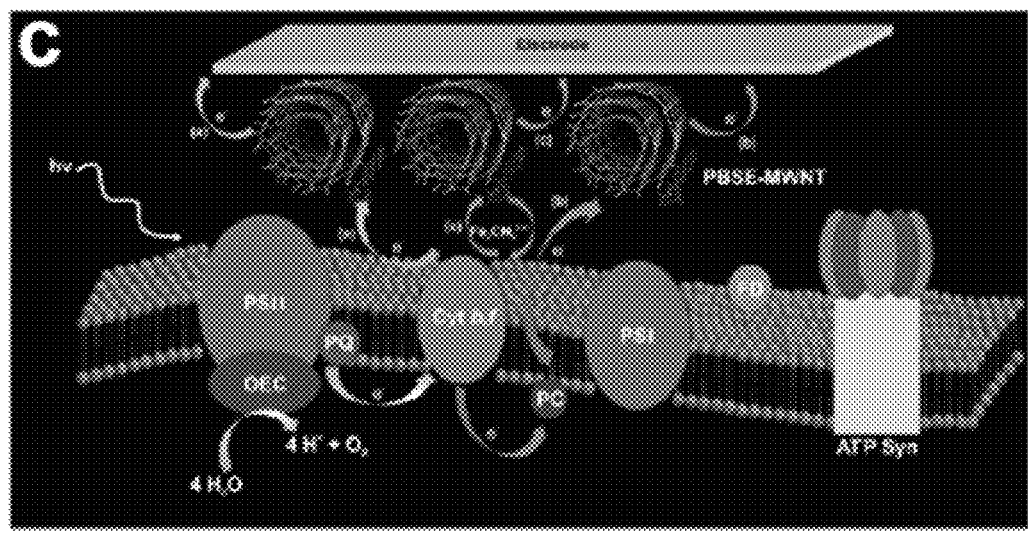
FIG. 9c is a block diagram of a thylakoid membrane immobilized on MWCNTs.

FIG. 9a is a block diagram of a chloroplast structure. FIG. 9b is a block diagram of an organization of photosystem II and light-harvesting complex II in the thylakoid membrane. FIG. 9c is a block diagram of a thylakoid membrane immobilized on MWCNTs. The leaf is a synergy of elaborated structures and functional components in order to produce highly complex machinery for photosynthesis—in which light harvesting, photo-induced charge separation, and catalysis modules combine to capture solar energy and efficiently split water into oxygen, H+ and a high energy electron. Chloroplasts enclose thylakoid membranes, which are the centers of the light-dependent photosynthesis reaction and are suspended in the chloroplast stroma, where food production occurs via the Calvin cycle (FIG. 9a). Specifically, the photosynthetic unit assembled in the thylakoid membrane consists of antenna pigments and reaction centers involving two photosystems (I & II). The absorption of light causes an electron to be ejected from the Chlorophyll reaction centers, which is then transferred vectorially via a pathway consisting of various mediators through a series of redox reactions from the inner to the outer section of the membrane (FIG. 9b). The photosynthetic reaction centers present in the thylakoids use the absorbed light energy to split H2O and generate O2, H+, a pH gradient, and high energy electrons (e−) with a quantum efficiency of nearly 100% (i.e., one quantum of light yields one electron transfer). The energy stored in the pH gradient and the high-energy e− is then used to reduce inorganic carbon to sugars and polysaccharides in the chloroplast stroma.

The exceptional quantum efficiency boasted by the primary reaction of the natural photosynthetic process has attracted significant interest for energy conversion applications. Attempts have been made to harvest the biomass stored as polysaccharide and convert it into ethanol, longer chain alcohols, or hydrogen. Microbial fuel cell systems are being developed for the generation of electricity through the oxidation of organic matter produced in microorganisms and plants. However, only a theoretical maximum of 27% of the solar energy absorbed by photosynthetic organisms can be converted into polysaccharide. In addition, the conversion of polysaccharides to forms of energy that can be readily used requires additional inputs and bioconversion processes that result in a substantial decrease in net energy yield. As an alternative, the extraction of the high energy e− from the photosynthetic electron transport chain (before fixing CO2 in the Calvin cycle) could lead to light energy conversion with higher efficiency. Interestingly, one study done with nanoelectrodes inserted into *Chlamydomonas reinhardtii* unicellular algal cells demonstrated the feasibility of this concept for direct extraction of photosynthetic electron. However, the utilization of whole photosynthetic cells (Mesophyll, cyanobacterial or algal cells) for this purpose suffers from the drawback of having respiration competing with photosynthesis in sharing the electron transfer pathways.

Furthermore, for direct light-electricity conversion applications, it is preferable to use a higher order plant based system that uses only water as the electron donor, such as PSII, rather than isolated PSI complexes, which require an alternate donor. However, when isolated plant photosynthetic systems are directly immobilized on electrodes, they suffer from low efficiencies due to degeneration of the biomolecules and poor electrical communication. In contrast, thylakoids, the photosynthetic organelles that perform the light-dependent reaction and house the reaction center complexes, offer the advantages of high individual protein stability, relatively simple immobilization procedures, and multiple electron transfer routes. A recent study involving immobilized thylakoid membranes on multi-walled carbon nanotubes (MWCNTs) proved the feasibility of the electron transfer from oxygen evolving complex (OEC) sites to the electrode achieved via various points in the electron transfer pathway, in addition to a direct transfer from PSII (FIG. 5c). Therefore, using thylakoids as photo-biocatalysts could offer the potential for high photo-electrochemical activity as well as high stability in energy conversion applications.

All of the previous attempts in exploiting the photosynthetic energy conversion of natural leaves focused only on the functional imitation, while neglecting the structural effect. In contrast, the creation of a bionic analog via the coupling of leaf-like hierarchical structures and analogous functional modules to perform the key steps of natural photosynthesis—capture of sunlight photons, oxidation of water to generate a high energy electron, and its conduction away from the reaction center—would be a major advance in the development of biomimetic systems for energy conversion. However, complete utilization of the photosynthetic functionality of the thylakoid functional components and efficient collection of bioelectricity, demands that any replicating engineered bionic system possess both hierarchical structures for efficient light-harvesting and analogous functional modules, which: i) transport the primary photosynthetic raw material, water, to the thylakoid lumen, and ii) transfer the electron generated via photolysis of water away from the reaction center in order to limit the wasteful recombination reactions, while synergistically, incorporating the efficient thylakoid-based natural photosynthetic engines.

It should be understood that the techniques disclosed above may be combined through the potential use of lasers for local and global heating as replacements or complement to the resistive electronic heating used here. The microfluidic-based photovoltaic functionality disclosed above was demonstrated via fabrication of a functional bionic leaf. Such features could be integrated towards future bionic organ fabrication (e.g. ear) given approaches could facilitate incorporation of vascular networks responsible for flow of biologic-supporting fluids and energy harvesting supporting fluids. Such functionality could also provide means of self-powering additional integrated bionic functionalities.

Fabrication Approach

Figure 10A:
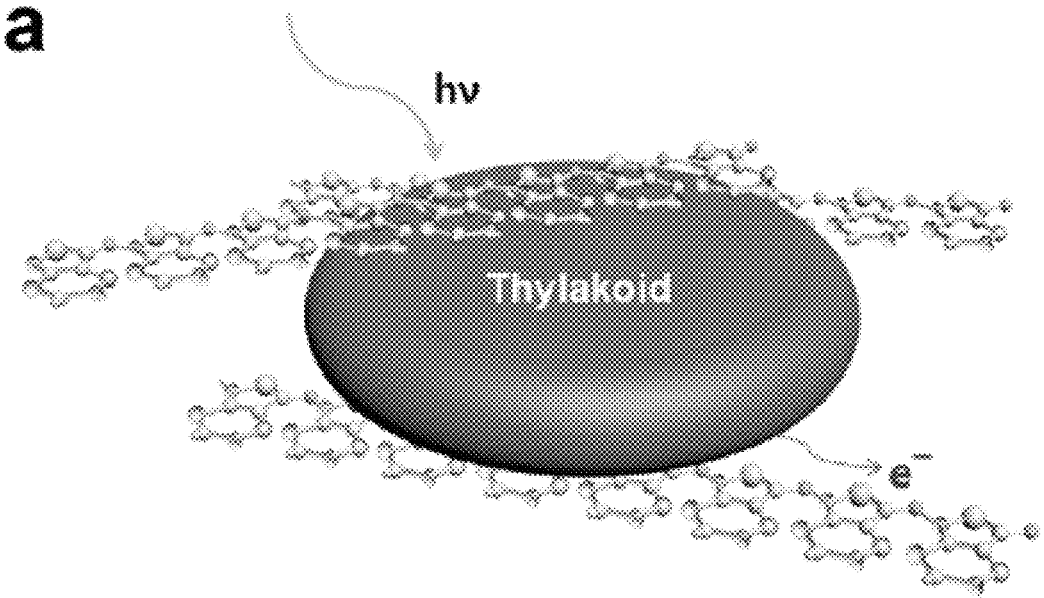
FIG. 10a is a block diagram of an electrical interfacing of thylakoid with a graphene nanoribbon/PEDOT:PSS conducting matrix.
Figure 10B:
FIG. 10b is a CAD drawing of a bionic leaf containing vasculature networks.
Figure 10C:
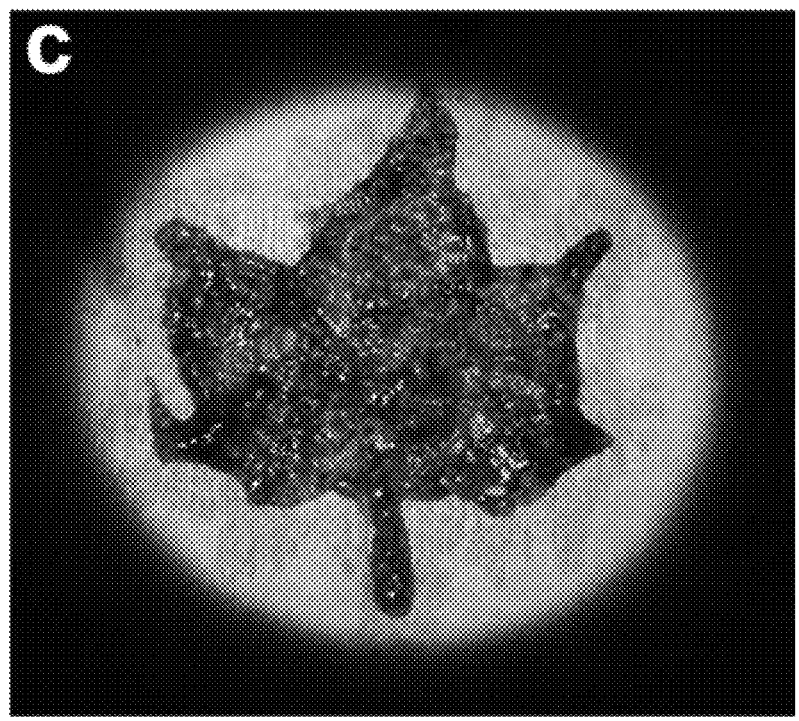
FIG. 10c is a photograph is a Thylakoid/PEDOT:PSS active photosynthetic matrix after 3D printing into a leaf architecture.

FIG. 10a is a block diagram of an electrical interfacing of thylakoid with a graphene nanoribbon/PEDOT:PSS conducting matrix. FIG. 10b is a CAD drawing of a bionic leaf containing vasculature networks. FIG. 10c is a photograph is a Thylakoid/PEDOT:PSS active photosynthetic matrix after 3D printing into a leaf architecture.

One approach involves the construction of a bionic leaf using 3D printing, by replicating the complex architecture of leaves, and incorporating engineered essential functional modules to realize efficient generation and harvesting of photosynthetic bioelectricity from thylakoid membranes. Specifically, isolated thylakoid photosynthetic functional units are assembled with interlaced graphene nanoribbons into a leaf-shaped hierarchical structure containing vascular networks for water flow, to realize efficient harvesting of light energy for photosynthetic e− generation and conduction. Electrical interfacing of the thylakoid membranes with organic polymers containing dispersed graphene nanoribbons allows for the collection of high-energy electrons from either the plastoquinone (PQ, acceptor side of PSII) pool or reduced ferredoxin (Fd, acceptor side of PSI), and transfer them through an external circuit (FIG. 10a). This enables generation of high efficiency bioelectricity via the extraction of high energy electrons before they are diverted toward $CO_2$ fixation and the reduction of macronutrients such as nitrite and sulfate. Further, it is possible to incorporate a 3D printed vasculature network that resembles the vascular bundles in natural leaves. These will include microchannels to provide water to the thylakoid lumen. Graphene nanoribbons may be used to provide transparent electrical contacts to transport generated electrons to an attached load. This approach potentially reduces recombination, as well as energy losses associated with the multistep transformation of solar energy into products used for the production of biodiesel and bioelectricity. By using the entire thylakoid membranes instead of isolated photosystem complexes in this design, it is possible to create electrical interfaces at various sites of the electron transfer pathways using a polymer/graphene nanoribbon matrix to achieve high electron transfer flux for photo-current generation.

Preliminary experiments involving the isolation, characterization and 3D printing of thylakoids have yielded promising results. Specifically, thylakoids were isolated from fresh organic spinach leaves according to previously reported procedures. In brief, the cleaned, deveined spinach leaves were homogenized in a chilled blender. The homogenate was then filtered through four layers of cheese cloth and the thylakoid membranes were then isolated from crude cell debris and other subcellular components after multiple steps of centrifugation at various speeds. The isolated thylakoids were characterized via optical and fluorescent microscopy using Nile red dye. The chlorophyll concentration in the isolated thylakoids was then determined by mixing with 80% acetone and filtering through filter paper followed by measuring the absorbance at 663 nm and 645 nm in a spectrophotometer. The chlorophyll concentration was calculated using Beer-Lambert law to be 2.799 mg/mL. Next, the photosynthetic functionality at the isolated thylakoid membranes was verified using the Hill reaction. Illumination of the Hill reagent mixed with thylakoids was found to be readily reduced, verifying the creation of photosynthetic electrons by the thylakoids in the presence of light. Next, the thylakoids were dispersed in a solution of PEDOT:PSS conductive polymer. A CAD drawing of the bionic leaf was then created (FIG. 10b), and the leaf architecture was 3D printed (FIG. 10c).

It should be understood that many variations are possible based on the disclosure herein. Although features and elements are described above in particular combinations, each feature or element can be used alone without the other features and elements or in various combinations with or without other features and elements.

What is claimed is:

1. A bioelectronic device comprising:
a scaffold formed via 3D printing; and
a bioelectronic component formed via 3D printing and comprising:
a cell-seeded matrix interwoven with the scaffold;
an insulating material; and
a conducting material.

2. The device of claim 1 wherein the scaffold is formed of at least one of synthetic polymers and natural biological polymers.

3. The device of claim 1 wherein the bioelectronic component comprises at least one of animal cells, plant cells, cellular organelles, proteins, DNA or RNA.

4. The device of claim 1 wherein the bioelectronic component is formed of laser curable materials.

5. The device of claim 1 wherein bioelectronic component is formed from a polymer.

6. The device of claim 1 wherein the bioelectronic component is formed from nano or micro-scale integrated electronic components.

7. The device of claim 1 wherein the scaffold is generally formed into the shape of an external animal anatomical feature.

8. The device of claim 1 wherein the scaffold is generally formed into the shape of internal animal or plant anatomical conduit.

9. The device of claim 1 wherein the scaffold is generally formed into the shape of plant structure.

10. The device of claim 1 wherein the bioelectronic component has electronic material properties that are modulated during printing via Peltier-based stage heating.

11. The device of claim 1 wherein the scaffold has structural and geometric features that are reduced to micron-scale via application of resistive heating of material syringes and extrusion tips.

12. The device of claim 1 the scaffold is cured via heat or light.

13. The device of claim 1 wherein the bioelectronic component comprises a semiconductor device.

14. The device of claim 13 wherein the semiconductor device is a light emitting diode.

15. The device of claim 1 wherein the bioelectronic device comprises a light harvesting structure formed via 3D printing.

16. The device of claim 1 wherein the bioelectronic device includes hydrogel-based conductive elements arranged into active capacitive components.

17. The device of claim 1 wherein the bioelectronic device include a piezoelectric element, (e.g, actuators, sensors, and printed robotics).

18. A method of forming a bioelectronic device, the method comprising:
    forming a scaffold via 3D printing;
    forming a bioelectronic component via 3D printing by printing:
        a cell-seeded matrix interwoven with the scaffold;
        an insulating material; and
        a conducting material.

19. A method of forming a bioelectronic device, the method comprising the steps of:
    providing a first component comprising a biological material;
    providing a second component comprising a conductive or semiconductive material;
    generating a bioelectronic construct by depositing at least the first component and the second component in one or more patterns defined by a predetermined print path.

20. The method of claim 19, further comprising the steps of:
    providing a third component comprising a biocompatible material adapted for supporting the bioelectronic device;
    depositing the third component in one or more patterns defined by a predetermined print path; and
    immersing the construct in a culture media.

21. The method of claim 20, further comprising the steps of:
    providing at least one additional component; and
    depositing the at least one component in one or more patterns defined by a predetermined print path.

* * * * *